United States Patent [19]

Schach et al.

[11] Patent Number: 5,504,264
[45] Date of Patent: Apr. 2, 1996

[54] PROCESS FOR PREPARING 1,3-DIFLUOROBENZENE

[75] Inventors: Thomas Schach, Gernsheim; Theodor Papenfuhs, Frankfurt am Main, both of Germany

[73] Assignee: Hoechst Artiengesellschaft, Germany

[21] Appl. No.: 360,190

[22] Filed: Dec. 20, 1994

Related U.S. Application Data

[63] Continuation of Ser. No. 154,257, Nov. 18, 1993, abandoned.

[30] Foreign Application Priority Data

Nov. 18, 1992 [DE] Germany .......................... 42 38 864.3

[51] Int. Cl.$^6$ ................................... C07C 25/13
[52] U.S. Cl. .......................................... 570/143
[58] Field of Search ............................... 570/143

[56] References Cited

FOREIGN PATENT DOCUMENTS 4224535 8/1992 Japan ..................................... 570/143

*Primary Examiner*—Alan Siegel
*Attorney, Agent, or Firm*—Connolly & Hutz

[57] ABSTRACT

Process for preparing 1,3-difluorobenzene by means of the catalytic elimination of halogen from a 1,3-difluorohalobenzene, by reacting a 1,3-difluorohalobenzene of the formula (1)

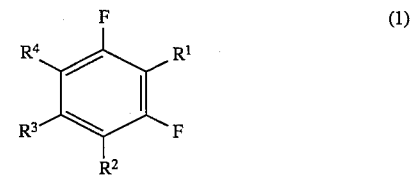

in which $R^1$ to $R^4$ are H, Cl or Br, and at least one of the radicals $R^1$ to $R^4$ is Cl or Br, in the presence of a palladium catalyst and of an amine, where appropriate in the presence of water or of an organic solvent which is inert towards the reactants and the reaction conditions, with hydrogen under pressure and at temperatures from about 70° to about 140° C.

25 Claims, No Drawings

PROCESS FOR PREPARING 1,3-DIFLUOROBENZENE

This application is a continuation of Ser. No. 08/154,257, filed Nov. 18, 1993, now abandoned.

The invention relates to an improved process for preparing 1,3-difluorobenzene by catalytic elimination of halogen from halogen-substituted 1,3-difluorobenzenes.

1,3-Difluorobenzene represents an important intermediate for preparing pharmaceutical products.

Processes for preparing 1,3-difluorobenzene are known per se. One of the known classical syntheses for preparing 1,3-difluorobenzene proceeds via 2,4-difluoronitrobenzene, which is reduced to the corresponding amine, diazotized and reductively boiled down. The industrial implementation of this process is problematical on account of the instability of the diazonium salts and the accumulation of acidic waste liquors which can only be disposed of with difficulty.

1,3-Difluorobenzene can also be prepared by means of direct Cl/F exchange on 1,3-dichlorobenzene. However, very drastic reaction conditions are required in this case and only moderate yields can be achieved (Pews, R. G.; Gall, J. A.; J. Fluorine Chem., 50 (3), 371-5; EP 371563).

An alternative preparation route proceeds via 3-fluoroaniline, which yields the desired 1,3-difluorobenzene by thermal decomposition following diazotization in the presence of hydrogen fluoride (JP 01283230).

More recently, preparation methods have been described which use 2,4-difluorobenzaldehyde as the precursor, the catalytic decarbonylation of which compound at high temperatures likewise represents an approach to the desired 1,3-difluorobenzene (DE 3935862; DE 3824141; U.S. Pat. No. 4847442).

The abovementioned, known processes in some cases provide only moderate yields or use starting compounds which are technically difficult to prepare and therefore expensive, Thus, in the case of the decarbonylation process, for example, the currently high price of the starting compound 2,4-difluorobenzaldehyde, corrosion problems, and the high catalyst costs, all make this process seem relatively unattractive for realization on an industrial scale.

In JP-A Hei-3-77836, a process is described for preparing 1,3-difluorobenzene by reductive dehalogenation of chloro-m-difluorobenzenes, such as, for example, 2,4-difluorochlorobenzene, using hydrogen gas in the presence of a catalyst and a base (as hydrogen chloride binder), with a platinum-support catalyst, a nickel-chromium-support catalyst or a Raney nickel-support catalyst being used as catalysts, and alkali metal hydroxides or carbonates, such as sodium or potassium hydroxide, or sodium or potassium carbonate, being used as the base (acid-capturing agent). However, narrow limits are imposed on the practical application of this process since, on the one hand, the reactions can only be reproduced with difficulty (see Comparative Examples 1 to 3) and, on the other, in addition to the corrosion problem, a product of only moderate quality (fluorobenzene content) can be achieved.

In view of the abovementioned disadvantages of the known processes, there was a great need for an improved process in which the inherent disadvantages in the known processes are avoided and where, in addition to good to very good yields and a very high degree of product purity, precursors are used which are readily accessible and available on an industrial scale.

It has now been found, surprisingly, that 1,3-difluorobenzene can be prepared in very good yields and at a very high level of purity, without noticeable corrosion of the reaction containers, by means of the elimination of halogen from a 1,3-difluorohalobenzene, by reacting a 1,3-difluorohalobenzene of the formula (1)

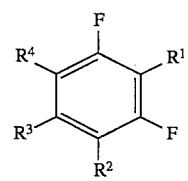

in which $R^1$ to $R^4$, independently of each other, are H, Cl or Br, and at least one of the radicals $R^1$ to $R^4$ is Cl or Br, in the presence of a palladium catalyst and of an amine or a mixture of different amines, where appropriate in the presence of water or of an organic solvent which is inert towards the reactants under the prevailing reaction conditions, with hydrogen under pressure and at temperatures from about 70° to about 140° C., preferably from about 90° to about 120° C., particularly preferably from about 95° to 115° C.

The starting compounds can be mixtures of a wide variety of chlorine- and/or bromine-substituted meta-difluorobenzenes. However, pure chlorine- or bromine-substituted meta-difluorobenzenes may also be employed. Individual representatives of the starting compounds of the said formula (1) which may be mentioned by way of example are a 1,3-difluorochlorobenzene, a 1,3-difluoro-dichlorobenzene, a 1,3-difluorobromobenzene or a 1,3-difluorodibromobenzene, such as, for example, 2,4-difluorochlorobenzene, 2,6-dichloro-1,3-difluorobenzene or 4,6-dichloro-1,3-difluorobenzene.

It is expedient to employ the catalyst on a support material, such as, for example, active charcoal, calcium carbonate, barium sulfate, pumice stone, alumina, diatomaceous earth, silica gel and/or aluminum oxide.

Preferably, use is made of palladium on active charcoal or aluminum oxide as the support material.

It is additionally expedient to use a palladium-support catalyst which contains about 0.1 to about 10% by weight, preferably about 0.2 to about 8% by weight, particularly preferably about 0.5 to about 6% by weight, of palladium, based on the whole catalyst.

About 10 to about 10,000 ppm of palladium are employed per mole of 1,3-difluorohalobenzene, and about 1 to about 50,000, preferably about 10 to about 10,000 ppm of palladium, based on equivalents of halogen which is to be eliminated.

Monoamines or polyamines having two to about four amino groups, or mixtures thereof, can be used as amines.

Those amines are particularly suitable which are of the formula (2)

$$NH_xR_y \qquad (2)$$

in which the R radicals, independently of each other, are a straight-chain or branched alkyl radical $—C_nH_{2n+1}$, in which n is a number from about 6 to about 20, preferably from about 7 to about 16, and particularly preferably from about 8 to about 12, x=0, 1 or 2, y=1, 2 or 3, and x+y=3.

Highly active aliphatic amines which may be mentioned specifically are tri-(N-dodecyl)amine and trialkyl ($C_8$–$C_{10}$) amines.

Although the abovementioned alkyl amines of the said formula (2) are the most suitable, in principle aryl amines and aralkyl amines may also be employed.

The amine concentration can be chosen at will. Preferably, the amine is used without the addition of a solvent or diluent.

With regard to the ratio of the quantities of amine and starting compound, it is expedient to carry out the reaction in the presence of about 50 to about 250 mol % of amine, based on equivalents of halogen to be eliminated.

3

Inert organic solvents which may be used, where appropriate, are, for example, toluene, xylenes, ethylbenzene, alkanols($C_1$–$C_4$), dialkyl($C_1$–$C_4$) ethers, tetrahydrofuran or polyethylene glycol dimethyl ethers having 1–15 ($C_1$–$C_4$) members.

As explained above, the reaction can also be carried out in the presence of water; in this case, however, it is preferable for the work to be carried out using a water content which is as low as possible (<1%, based on the reaction solution).

The process can be carried out both under atmospheric pressure and under excess pressure. It is expedient to carry out the reaction at a hydrogen pressure of about 0.1 to about 50 bar.

The process can be carried out within the abovementioned general and preferred temperature ranges. The use of temperatures which are too low results in a reaction which is slow and incomplete. If temperatures are selected which are too high, this can bring about unwanted elimination of fluoride.

The process according to the invention can be carried out in the presence or absence of atmospheric oxygen. Working under a protective gas atmosphere is preferred, with nitrogen or argon being used as the protective gas.

In addition to hydrogen, other reducing agents which can act as hydrogen suppliers, such as, for example, alcohols, glycols, formates and hydrazine hydrate, can also be used as reducing agents.

For regeneration purposes, the amine hydrohalide accumulating during the course of the reaction is treated with an inorganic base, such as, for example, sodium hydroxide solution or magnesium oxide. For this reason, it is expedient that neither the free amine nor its hydrohalide is water-soluble, so that resultant working-up problems are avoided.

The starting compounds which are employed in the process according to the invention and are of the said formula (1) can be prepared by treating a nitro-meta-difluorobenzene or a mixture of different nitro-meta-di-fluorobenzenes or nitro-meta-difluorohalobenzenes of the formula (3)

$$m\text{–}(F)_2\text{–}Ar\text{–}(NO_2)_z R_k \qquad (3)$$

in which R=Cl or Br, z=1 or 2 and k=0, 1 or 2, with chlorine gas in the absence of Lewis acids at temperatures from about 80° to about 250° C.

Further details with regard to the preparation of these starting compounds are as follows:

The chlorine gas which is used is employed in anhydrous form. The reaction of the m-difluoronitro-aromatic compounds with the chlorine must be carried out in the absence of Lewis acids or other chlorinating catalysts. The required temperatures are within the range from 80° to 250° C. preferably 100° to 200° C. The reaction can be carried out in the presence or absence of a fluoride-capturing agent. The necessary chlorodifluorobenzene compound (starting compound) can, for example, be prepared as follows: 1800 g (11.3 mol) of 2,4-difluoronitrobenzene (anhydrous and free of Lewis acids) are initially introduced into a 2 l four-neck flask having a stirrer, gas-entry tube and distillation bridge. The reaction solution is brought to 160° C. A stream of chlorine of 4–6 l/h is then passed through the solution at this temperature. After 1–2 h, brown gases are formed which are absorbed in dilute sodium hydroxide solution. After 28 h, the entry of gas is stopped and the reaction solution is distilled (head temperature 127° C). 675.8 g of 2,4-difluorochlorobenzene are obtained, corresponding to a yield of 91%, based on reacted 2,4-difluoronitrobenzene.

The Examples below serve to illustrate the process according to the invention without limiting it thereto.

4

EXAMPLE 1

To prepare 1,3-difluorobenzene, 148.5 g (1.0 mol) of 2,4-difluorochlorobenzene, 4.0 g of Pd/C (5% strength, 50% moisture content), as the catalyst, and 626.4 g (1.2 mol) of tri-(N-dodecyl)amine, as the base, are initially introduced into the reaction vessel (autoclave). The reaction solution is heated to 100° C. and reductively dechlorinated with hydrogen at this temperature. Once hydrogen uptake is complete, the mixture is briefly stirred and cooled to 50°–60° C., and the reaction solution is extracted by shaking with sodium hydroxide solution and the catalyst is filtered off with suction from the reaction mixture. Once the organic phase has been separated off, it is distilled under atmospheric pressure and the resultant distillate is dried and then fractionated. Remaining mother liquor, first runnings, intermediate cuts and distillation residues can be reintroduced in subsequent batches.

| | |
|---|---|
| Conversion: | 92.1% (according to GC) |
| Yield: | 97.1 g (0.85 mol) of 1,3-difluorobenzene |
| | 85.2%, based on 2,4-difluorochlorobenzene employed |
| Purity: | 0.2 (GC % area) of unknown compounds |
| | 99.7 (GC % area) of 1,3-difluorobenzene |
| | 0.1 (GC % area) of fluorobenzene |
| Corrosion: | material investigations at 100° C. |
| | 1.4439 removed material: <0.01 mm/a |
| | 1.4571 removed material: <0.01 mm/a |

EXAMPLE 2

To prepare 1,3-difluorobenzene, 267.3 g (1.8 mol) of 2,4-difluorochlorobenzene, 4.1 g of Pd/C (5% strength, 50% moisture content), as the catalyst, and 871.2 g (2.2 mol) of a mixture of trialkyl($C_8$–$C_{10}$)amines, as the base, are initially introduced into the reaction vessel (autoclave). The reaction solution is heated to 100° C. and reductively dechlorinated with hydrogen at this temperature. Once hydrogen uptake is complete, the mixture is briefly stirred and then cooled down to room temperature, and the reaction solution is then extracted by shaking with sodium hydroxide solution and the catalyst is filtered off with suction from the reaction mixture. Once the organic phase has been separated off, it is distilled under atmospheric pressure and the resulting distillate is dried and then fractionated. Remaining mother liquor, first runnings, intermediate cuts and distillation residues can be reintroduced in subsequent batches.

| | |
|---|---|
| Conversion: | 96.0% (according to GC) |
| Yield: | 186.7 g (1.64 mol) |
| | 91.4%, based on 2,4-difluorochlorobenzene employed |
| Purity: | 99.9 (GC % area) of 1,3-difluorobenzene |
| | 0.05 (GC % area) of fluorobenzene |
| Corrosion: | material investigations at 100° C. |
| | 1.4439 removed material: <0.01 mm/a |
| | 1.4529 removed material: <0.01 mm/a |

Comparison Example 1

To prepare 1,3-difluorobenzene, 415 g (2.8 mol) of 2,4-difluorochlorobenzene, 10 g of Pd/C (5% strength, 50% moisture content) and 120 g of NaOH are initially introduced into the reaction vessel (autoclave) in 500 ml of water. The mixture of the reaction components is slowly heated to 100° C. in the presence of hydrogen. The reaction suspension is maintained at this temperature until no further uptake of hydrogen (reductive dechlorination) can be observed.

Subsequently, the catalyst is separated off from the reaction mixture and the organic phase is subjected to fractional distillation.

| Conversion: | 85.3% (according to GC) |
|---|---|
| Yield: | 206.2 g (1.8 mol) of 1,3-difluorobenzene |
| | 64.6%, based on 2,4-difluorochlorobenzene employed |
| Purity: | 0.2 (GC % area) of unknown compounds |
| | 99.2 (GC % area) of 1,3-difluorobenzene |
| | 0.6 (GC % area) of fluorobenzene |

Comparison Example 2

Reaction in analogy with Comparison Example 1. The reaction solution was maintained at 100° C. for 1 hour. No uptake of hydrogen takes place.
Conversion: 4.5% (according to GC)

Comparison Example 3

Fresh catalyst is added to the reaction solution from Comparison Example 2, which is heated once again to 100° C. in the presence of hydrogen. However, no conversion takes place. Subsequently, the temperature is raised to 120° C., when a reaction slowly commences but then stops after about 2 hours. There is only a small uptake of hydrogen.
Conversion: 30.2% (according to GC)

Comparison Example 4

To prepare 1,3-difluorobenzene, 297.1 g (2.0 mol) of 2,4-difluorochlorobenzene, 6.0 g of Pd/C (5% strength, 50% moisture content) and 212.5 g of 25% strength ammonia are initially introduced into the reaction vessel (autoclave). The mixture of the reaction components is heated 105° C. and treated with hydrogen at this temperature. Once hydrogen uptake is complete, the catalyst is filtered off with suction from the reaction mixture and the organic phase is separated off and subjected to fractional distillation.

| Conversion: | 94.6% (according to GC) |
|---|---|
| Yield: | 182.9 g (1.6 mol) of 1,3-difluorobenzene |
| | 80.2%, based on 2,4-difluorochlorobenzene employed |
| Purity: | 0.3 (GC % area) of unknown compounds |
| | 99.2 (GC % area) of 1,3-difluorobenzene |
| | 0.5 (GC % area) of fluorobenzene |

Comparison Example 5

The reaction of Comparison Example 4 is repeated under identical conditions. However, there is no uptake of hydrogen at 105° C. The reductive dehalogenation is only rendered possible by raising the reaction temperature to 140° C.

| Conversion: | 68.0% (according to GC) |
|---|---|
| Yield: | 123.1 g (1.1 mol) of 1,3-difluorobenzene |
| | 54.0%, based on 2,4-difluorochlorobenzene employed |
| Purity: | 0.2 (GC % area) of unknown compounds |
| | 99.2 (GC % area) of 1,3-difluorobenzene |
| | 0.6 (GC % area) of fluorobenzene |

Comparison Example 6

To prepare 1,3-difluorobenzene, 594.1 g (4.0 mol) of 2,4-difluorochlorobenzene, 11.9 g of Pd/C (5% strength, 50% moisture content) and 89.0 g (2.2 mol) of MgO are initially introduced into the reaction vessel (autoclave) in 450 ml of water. The mixture of the reaction components is heated to 140° C. and reductively dechlorinated with hydrogen at this temperature. Once hydrogen uptake is complete, the catalyst is filtered off with suction from the reaction mixture and the organic phase is separated off and subjected to fractional distillation.

| Conversion: | 96.4% (according to GC) |
|---|---|
| Yield: | 388.5 g (3.4 mol) of 1,3-difluorobenzene |
| | 85.2%, based on 2,4-difluorochlorobenzene employed |
| Purity: | 0.2 (GC % area) of unknown compounds |
| | 99.6 (GC % area) of 1,3-difluorobenzene |
| | 0.2 (GC % area) of fluorobenzene |
| Corrosion: | material investigations at 140° C. |
| | 1.4439 tension crack corrosion |
| | 1.4571 tension crack corrosion |

Comparison Example 7

Reaction took place in analogy with Comparison Example 6. The reductive dehalogenation was carried out at 120° C. (There is no reaction at 100° C.)

| Conversion: | 91.4% (according to GC) | |
|---|---|---|
| Yield: | 369.4 g (3.2 mol) | |
| | 81.0%, based on 2,4-difluorochlorobenzene employed | |
| Purity: | 0.2 (GC % area) of unknown compounds | |
| | 99.6 (GC % area) of 1,3-difluorobenzene | |
| | 0.2 (GC % area) of fluorobenzene | |
| Corrosion: | material investigations at 120° C. | |
| | 1.4439 removed material: | 2.0 mm/a |
| | 1.4529 removed material: | 1.6 mm/a |
| | 2.4856 removed material: | 0.6 mm/a |
| | 2.4858 removed material: | 1.2 mm/a |

Comparison Example 8

To prepare 1,3-difluorobenzene, 572.0 g ( 3.85 mol ) of 2,4-difluorochlorobenzene, 11.9 g of Pd/C (5% strength, 50% moisture content) and 95.8 g (4.0 mol) of LiOH are initially introduced into the reaction vessel (autoclave) in 400 ml of water. The mixture of the reaction components is heated to 100° C. and reductively dechlorinated with hydrogen at this temperature. Once hydrogen uptake is complete, the catalyst is filtered off with suction from the reaction mixture and the organic phase is separated off and subjected to fractional distillation.

| Conversion: | 79.9% (according to GC) |
|---|---|
| Yield: | 308.2 g (2.7 mol) of 1,3-difluorobenzene |
| | 70.2%, based on 2,4-difluorochlorobenzene employed |
| Purity: | 0.2 (GC % area) of unknown compounds |
| | 99.6 (GC % area) of 1,3-difluorobenzene |
| | 0.2 (GC % area) of fluorobenzene |

We claim:

1. A process for preparing 1,3-difluorobenzene of high purity comprising catalytic elimination of halogen from a 1,3-difluorohalobenzene, wherein said 1,3-difluorohalobenzene of the formula (1)

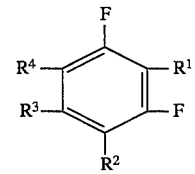

in which $R^1$ to $R^4$, independently of each other, are H, Cl or Br, and at least one of the radicals $R^1$ to $R^4$ is Cl or Br, or mixtures of 1,3-difluorohalobenzes of the said formula, is/are reacted, in the presence of a palladium catalyst and of an amine or of a mixture of different amines, and optionally in the presence of water or of an organic solvent which is inert towards the reactants and the reaction conditions, with hydrogen under at least 0.1 bar pressure and at temperatures from about 70° to about 140° C.

2. The process as claimed in claim 1, wherein mixtures of 1,3-difluorohalobenzenes of the formula (1) mentioned in claim 1 are reacted.

3. The process as claimed in claim 1, wherein a 1,3-difluorochlorobenzene, a 1,3-difluorodichlorobenzene, a 1,3-difluorobromobenzene or a 1,3-difluorodibromobenzene or a mixture thereof is reacted.

4. The process as claimed in claim 1, wherein 2,4-difluorochlorobenzene, 2,6-dichloro-1,3-difluorobenzene or 4,6-dichloro-1,3-difluorobenzene is reacted.

5. The process as claimed in claim 1, wherein the reaction is carried out at temperatures from about 90° to about 120° C.

6. The process as claimed in claim 1, wherein the reaction is carried out at temperatures from about 95° to about 115° C.

7. The process as claimed in claim 1, wherein a palladium-support catalyst is employed as the palladium catalyst.

8. The process as claimed in claim 1, wherein the support material of the palladium catalyst comprises pumice stone, alumina, calcium carbonate, barium sulfate, diatomaceous earth, silica gel, aluminum oxide or active charcoal or a mixture thereof.

9. The process as claimed in claim 1, wherein the support material of the palladium catalyst comprises aluminum oxide or active charcoal or a mixture thereof.

10. The process as claimed in claim 1, wherein the palladium catalyst contains about 0.1 to about 10% by weight of palladium, based on the whole catalyst.

11. The process as claimed in claim 1, wherein the palladium catalyst contains about 0.2 to about 8% by weight of palladium, based on the whole catalyst.

12. The process as claimed in claim 1, wherein the palladium catalyst contains about 0.5 to about 6% by weight of palladium, based on the whole catalyst.

13. The process as claimed in claim 1, wherein about 1 to about 50,000 ppm of palladium, based on equivalents of halogen to be eliminated, are employed.

14. The process as claimed in claim 1, wherein about 10 to about 10,000 ppm of palladium are employed per mole of 1,3-difluorohalobenzene.

15. The process as claimed in claim 1, wherein a monoamine or a polyamine having 2 to about 4 amino groups, or mixtures thereof, is/are employed as the amine.

16. The process as claimed in claim 1, wherein the reaction is carried out in the presence of an amine of the formula $$NH_xR_y$$

in which the R radicals, independently of each other, are a straight-chain or branched alkyl radical —$C_nH_{2n+1}$, in which n is a number from about 6 to about 20, x=0,1 or 2, y=1,2 or 3 and x+y=3.

17. The process as claimed in claim 16, wherein n is a number from about 7 to about 16.

18. The process as claimed in claim 16, wherein n is a number from about 8 to about 12.

19. The process as claimed in claim 1, wherein the reaction is carried out in the presence of tri-(N-dodecyl)amine.

20. The process as claimed in claim 1, wherein the reaction is carried out in the presence of trialkyl ($C_8$–$C_{10}$) amines.

21. The process as claimed in claim 1, wherein the reaction is carried out in the presence of about 50 to about 250 mol % of amine, based on equivalents of halogen to be eliminated.

22. The process as claimed in claim 1, wherein the reaction is carried out in the presence of toluene, xylenes, ethylbenzene, alkanols($C_1$–$C_4$), dialkyl($C_1$–$C_4$) ethers, tetrahydrofuran or polyethylene glycol dimethyl ethers having 1–15 ($C_1$–$C_4$) members as the inert organic solvent.

23. The process as claimed in claim 1, wherein the reaction is carried out under atmospheric pressure.

24. The process as claimed in claim 1, wherein the reaction is carried out under excess pressure.

25. The process as claimed in claim 1, wherein the reaction is carried out at a hydrogen pressure of about 0.1 to about 50 bar.

* * * * *